United States Patent [19]

Landis

[11] Patent Number: 4,708,013

[45] Date of Patent: Nov. 24, 1987

[54] LIQUID WATER CONTENT ANALYZER

[76] Inventor: Dwight A. Landis, P.O. Box 8062, Calabasas, Calif. 91302

[21] Appl. No.: 9,502

[22] Filed: Feb. 2, 1987

[51] Int. Cl.[4] .................... G01N 30/66; G01N 30/70
[52] U.S. Cl. ........................................... 73/23.1; 73/29
[58] Field of Search ................................. 73/23.1, 29

[56] References Cited

U.S. PATENT DOCUMENTS

| 3,753,653 | 8/1973 | Brieva et al. | 73/23.1 X |
| 4,215,563 | 8/1980 | Clardy et al. | 73/23.1 |
| 4,403,503 | 9/1983 | Banerjee et al. | 73/23.1 X |

*Primary Examiner*—Stewart J. Levy
*Assistant Examiner*—Joseph W. Roskos
*Attorney, Agent, or Firm*—John J. Deinken

[57] ABSTRACT

A method of measuring the amount of liquid water in an aerosol begins with removing adsorbed water and water vapor from a sample chamber. A first sample flow of the aerosol is directed through the sample chamber at a first flow rate for a first time period, then the liquid and solid components of the sample are separated from the gaseous components in the sample chamber. The liquid components of the first sample are evaporated from the sample chamber by directing a flow of a carrier gas through the sample chamber. The water vapor is separated from the evaporated components of the first sample and the quantity of water vapor is measured. Adsorbed water and water vapor is removed from a reference chamber which is substantially identical to the sample chamber. The liquid and solid components are then separated from the gaseous components of a second sample flow of the aerosol and the gaseous components of the second sample are directed through the reference chamber at a second flow rate for a second time period. The liquid components are evaporated from the reference chamber by directing a flow of a carrier gas through the reference chamber and the quantity of water vapor in the carrier gas from the reference chamber is measured. The amount of liquid water in the aerosol is then determined by subtracting the amount of water measured in the reference chamber carrier gas from the amount of water measured in the sample chamber carrier gas.

13 Claims, 1 Drawing Figure

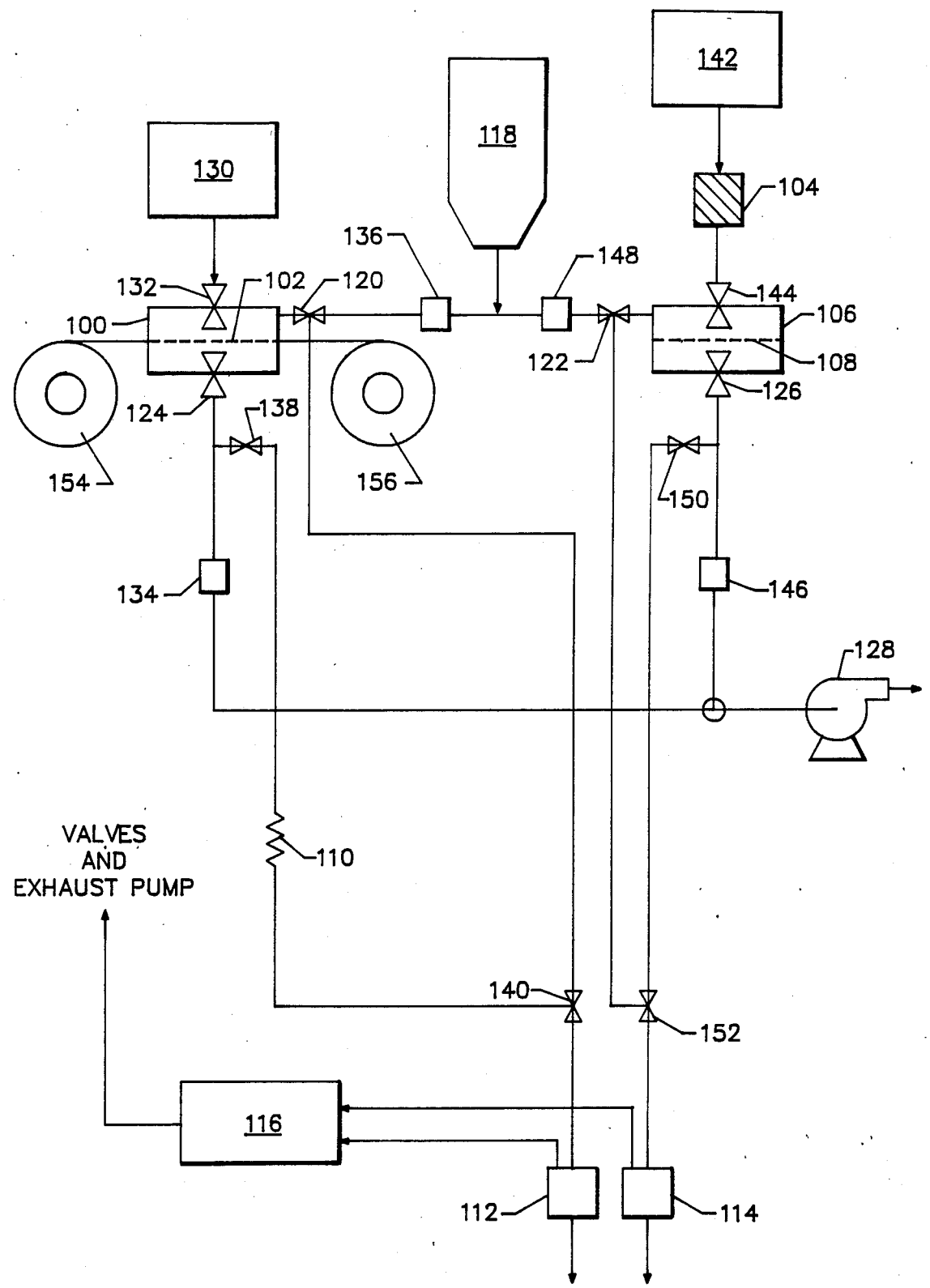

LIQUID WATER CONTENT ANALYZER

BACKGROUND OF THE INVENTION

This invention is concerned with a techniqu determining the liquid water content of an ambient aerosol.

An ambient aerosol is composed of a variety of chemical components which influence the behavior of the aerosol in the atmosphere. Some species of these components are chemically reactive with other gas phase components, resulting in changes in aerosol size and chemical composition over time. Other compounds found in ambient aerosols, such as hygroscopic inorganic salts (sodium chloride and ammonium sulfate, for example), are chemically stable but may cause changes in size and composition due to their tendency to adsorb water vapor from the surrounding air. These size changes can become significant at high (greater than 70%) relative humidities, resulting in increased light scattering and reduced visibility. In order to adequately assess the importance of liquid water to aerosol chemistry, it is necessary to determine the amount of free (chemically unbound) water in ambient aerosols. To date, no instrument available in the art has been capable of making these measurements over a broad range of ambient temperatures and relative humidities.

A direct, quantitative measurement of the liquid water content of an aerosol is very difficult to make, because under some conditions this value may be very small (less than 10 ug/m$^3$ (micrograms per cubic meter), for example) with a much larger amount of water vapor contained in the surrounding air (19 g/m$^3$ (grams per cubic meter), for example, for saturated air at 70°). Ideally, the measurement of liquid water content should be made in situ, using an instrument which can differentiate liquid water from water vapor with a precision approaching 0 ug/m$^3$. Several attempts have been made to determine aerosol liquid water content under these conditions. None of the instruments in the prior art, however, has proven capable of accurately making these measurements over a realistic range of ambient temperatures, relative humidities, and aerosol concentrations.

SUMMARY OF THE INVENTION

The liquid water content analyzer of this invention uses gas chromatography to determine the total amount of water in an aerosol sample. The analyzer consists of a dual channel filter sampler with a thermal conductivity or electron capture detector. An aerosol sample is introduced to the analyzer through an inlet and is deposited on a filter tape located inside the sample chamber. The liquid moisture is removed from the aerosol by the filter, then passed through a separating column. A thermal conductivity detector or electron capture detector is used to provide a quantitative analysis of the moisture content passing through the separating column. The adsorbent water vapor on the filter is determined in order to measure the net aerosol liquid water content. Gas chromatography is attractive because it is specific for water, can be easily automated, and is a very sensitive, well demonstrated analytical technique.

An aerosol analyzer constructed according to this invention includes a sample chamber for receiving a first sample flow of an aerosol, with a sample filter in the sample chamber for separating the liquid and solid components of the first sample from the gaseous components of the first sample. A preliminary filter separates the liquid and solid components of a second sample flow of the aerosol from the gaseous components of the second sample. A reference chamber is substantially identical to the sample chamber and receives a flow of the gaseous components of the second sample. A reference filter substantially identical to the sample filter is positioned in the reference filter. A source of a carrier gas is used for evaporating the liquid components of the first sample from the sample chamber and for evaporating any liquid components from the reference chamber. A chromatographic separation column separates the water vapor from the evaporated components of the first sample and a detector measures the quantity of water separated by the separation column and the quantity of water evaporated from the reference chamber.

In more particular embodiments, the detector is either a thermal conductivity detector or an electron capture detector. In addition, the detector may be used only for measuring the quantity of water separated by the separation column, while a second detector is provided for measuring the quantity of water evaporated from the reference chamber. The analyzer may further include a microprocessor for comparing the amount of water measured in the sample chamber to the amount of water measured in the reference chamber to determine the amount of liquid water in the aerosol. Mass flow controllers may be used for controlling the rate of the first sample flow through the sample chamber, for controlling the rate of the second sample flow through the reference chamber, for controlling the rate of the flow of the carrier gas through the sample chamber, and for controlling the rate of the flow of the carrier gas through the reference chamber. The analyzer may also include an exhaust pump for drawing the first sample flow through the sample chamber and for drawing the second sample flow through the reference chamber.

A method of measuring the amount of liquid water in an aerosol, according to this invention, begins by directing a first sample flow of the aerosol through a sample chamber at a first flow rate for a first time period and separating the liquid and solid components from the gaseous components of the first sample in the sample chamber, then measuring the quantity of water contained in the sample chamber. The liquid and solid components are separated from the gaseous components of a second sample flow of the aerosol, then the gaseous components are directed through the reference chamber at a second flow rate for a second time period. The quantity of water contained in the reference chamber is measured and subtracted from the amount of water measured in the sample chamber to determine the amount of liquid water in the aerosol.

In more particular embodiments, the step of separating the liquid and solid components from the gaseous components of the first sample in the sample chamber involves providing a sample filter in the sample chamber for separating the liquid and solid components of the first sample from the gaseous components of the first sample and a reference filter, substantially identical to the sample filter, in the reference chamber. The step of measuring the quantity of water contained in the sample chamber may be accomplished by evaporating the liquid components of the first sample from the sample chamber with a carrier gas, separating the water vapor from the evaporated components of the first sample with a chromatographic separation column, and measuring the quantity of water separated by the separation column. The step of measuring the quantity of water contained in the reference chamber may be achieved by evaporating any liquid components in the reference chamber with a carrier gas and measuring the quantity of water in the evaporated liquid components.

DESCRIPTION OF THE DRAWINGS

The drawing figure is a schematic diagram depicting a liquid water analyzer constructed according to the present invention.

DESCRIPTION OF THE INVENTION

The schematic diagram in the drawing depicts a preferred embodiment of the liquid water analyzer of this invention. The major components of the analyzer include a sample chamber 100, a sample filter 102, a preliminary filter 104, a reference chamber 106, a reference filter 108, a chromatographic separation column 110, a sample chamber detector 112, a reference chamber detector 114, and a microprocessor controller 116. The analyzer is designed to measure the amount of liquid water in an aerosol. The measurement procedure begins with a purge of the sample and reference chambers to remove any latent adsorbed water and water vapor. The purge is accomplished by directing an inert carrier gas from a pressurized gas reservoir 118 into the sample chamber via a valve 120 and into the reference chamber by means of a valve 122. The purging gas is removed from the chambers through valves 124 and 126. In the preferred embodiment, all of the valves in the apparatus are opened and closed automatically under the control of the microprocessor controller 116, which also integrates and stores data from the detectors 112 and 114.

After the apparatus has been purged, a first sample 130 of the aerosol is then introduced into the sample chamber 100 by means of a valve 132. The first sample is drawn through the chamber and exits through the valve 124 due to the operation of an exhaust pump 128, which is also controlled by the controlled 116. A mass flow controller 134 accurately determines the flow rate of the sample. As the first sample traverses the sample chamber 100, the filter 102 traps and holds the liquid and solid components in the sample. This filter must employ a hydrophobic filter media to reduce the amount of adsorbent water vapor. In addition, the filter must be sufficiently porous to allow a high sampling flow rate and high collection efficiency for submicron particles.

After the first sample has completed its flow through the sample chamber, a flow of the carrier gas is directed through the sample chamber by means of valves 120 and 124 to evaporate the liquid components of the first sample from the sample chamber and the filter 102 and entrain those components in the carrier gas. The flow rate of the carrier gas is accurately controlled by a mass flow controller 136. This quantity of carrier gas is then directed through the chromatographic separation column 110 by means of a valve 138. The separation column passes different components of the carrier gas at different rates. By this means, the water vapor in the carrier gas is separated from the remaining components of the gas in the downstream flow from the separation column. By detecting the water peak as it eludes from the column, a specific determination of the aerosol liquid water can be obtained. This chromatographic technique is well known in the art and need not be discussed in any further detail here.

The elutant from the separation column is conveyed via a valve 140 to the detector 112, which provides a quantitative measure of the amount of water vapor contained in the stream of carrier gas from the separation column. This detector may be a thermal conductivity or electron capture type of detector. Either detector will exhibit adequate sensitivity. A thermal conductivity detector requires a reference flow and an electrical bridge to detect changes in the composition of the sample flow stream, while an electron capture detector requires only one flow path. The operation of such detectors is conventional and well known in the art and thus will not be discussed in any further detail here.

A second, parallel reference sampling function can be carried out concurrently with that just described. This operation begins with a second sample 142 of the aerosol, from which the liquid and solid components are removed by the preliminary filter 104. The second sample of the aerosol is filtered to allow only clean air at ambient relative humidity to flow through the reference side. The gaseous components of the second sample are then introduced into the reference chamber 106 by means of a valve 144. The sample and reference chambers must be identical and designed with a very small volume in order to minimize the amount of ambient water vapor trapped during the purge cycle. The reference chamber contains the reference filter 108, which is identical to the sample filter 102, to ensure that the sample passing through the reference chamber is subjected to the same conditions as the first sample experiences in the sample chamber. The second sample is conveyed out of the reference chamber by means of the valve 126 and the exhaust pump 128. A mass flow controller 146 provides control over the rate at which the second sample is flowed through the reference chamber. The carrier gas is then directed, by means of the valve 122 and under the control of a mass flow controller 148, through the reference chamber to evaporate any water which may have collected in the chamber. This quantity of the carrier gas is then passed, via the valve 126, a valve 150, and a valve 152, to the reference chamber detector 114, which is similar to the sample chamber detector 112. The second detector provides a quantitative indication of the amount of water vapor present in the carrier gas. Using inputs from the detectors 112 and 114, the timing of the opening and closing of the various valves, and known rates of flow provided by the mass flow controllers in the apparatus, the microprocessor controller 116 compares the amount of water measured in the sample chamber carrier gas to the amount of water measured in the reference chamber carrier gas to determine the amount of liquid water which was present in the sampled aerosol. Since the sample and reference chambers are identical, moisture removed from the filter and walls will be the same for each chamber. Therefore, the difference in the signals will be proportional to the amount of free water which was present in the aerosol sample.

In the preferred embodiment, the analyzer is equipped to perform automatic, continuous sampling. A silanized glass fiber filter is used because of its low moisture retention coupled with a high flow rate and high efficiency. This filter can be used in tape form, with the fresh portion of the filter stored on a supply reel 154, while the used portion is retained on a storage reel 156. After a one hour sampling period, the inlet and outlet valves to each chamber are automatically closed and each side is purged with dry helium to remove moisture from the aerosol deposit, filter, and sample chamber walls. The flow rate through each chamber is regulated with mass flow controllers. The sample chamber will sample at a nominal 0.28 m³/min flow rate. The flow through the reference chamber may be less since it is only used for subtracting the adsorptive water on the filter and chamber walls. Therefore, it is only necessary to flow enough air to provide equilibrium moisture conditions. At the end of the analysis cycle, the controller 116 moves the filter tape to a new position, the purge valves are closed, and the inlet and outlet valves are opened to begin a new sampling cycle. A clean filter is necessary for each cycle since dried hygroscopic particles from a previous sampling cycle will adsorb water vapor.

The worst sampling case would involve an aerosol containing a small amount of adsorptive moisture (assume, e.g., 10 ug/m³) at a high (95%) relative humidity. Under these conditions, the air contains about 19 ug/cm³ of water vapor at 70° F. Assuming a sample chamber volume of 5 cm³, 95 ug of water vapor will be sealed in the chamber during the purge cycle. If the instrument samples at a flow rate of 0.28 m³/min, approximately 160 ug of liquid water will be collected on the filter. Assuming an additional 50 ug of water will adsorb on the filter and chamber walls, a signal to noise ratio of approximately 1 can be obtained. The actual value will be higher, however, because the reference chamber will cancel the background signal in the sample flow.

The preferred embodiments of this invention have been illustrated and described above. Modifications and additional embodiments, however, will undoubtedly be apparent to those skilled in the art. Although one design for a continuously replaceable filter is described, for example, another option would be to use sintered stainless disks in a cassette mechanism which could be changed after each sampling cycle. Also, if the flows through the sample and reference chambers were sequentially purged, only one detector would be required and could be used for water detection from both sides of the analyzer. Furthermore, equivalent elements may be substituted for those illustrated and described herein, parts or connections might be reversed or otherwise interchanged, and certain features of the invention may be utilized independently of other features. Consequently, the exemplary embodiments should be considered illustrative, rather than inclusive, while the appended claims are more indicative of the full scope of the invention.

I claim:

1. An aerosol analyzer, comprising:
   a sample chamber for receiving a first sample flow of an aerosol;
   a sample filter in the sample chamber for separating the liquid and solid components of the first sample from the gaseous components of the first sample;
   a preliminary filter for separating the liquid and solid components of a second sample flow of the aerosol from the gaseous components of the second sample;
   a reference chamber substantially identical to the sample chamber for receiving a flow of the gaseous components of the second sample;
   a reference filter in the reference chamber substantially identical to the sample filter;
   a source of a carrier gas for evaporating the liquid components of the first sample from the sample chamber and for evaporating any liquid components and adsorbed water vapor from the reference chamber;
   a chromatographic separation column for separating the water vapor from the evaporated components of the first sample; and
   a detector for measuring the quantity of water separated by the separation column and the quantity of water evaporated from the reference chamber.

2. The analyzer of claim 1, further comprising a microprocessor for comparing the amount of water measured in the sample chamber to the amount of water measured in the reference chamber to determine the amount of liquid water in the aerosol.

3. The analyzer of claim 1, wherein the detector further comprises a first detector for measuring the quantity of water separated by the separation column and further comprising a second detector for measuring the quantity of water evaporated from the reference chamber.

4. The analyzer of claim 1, further comprising:
   a first mass flow controller for controlling the rate of the first sample flow through the sample chamber; and
   a second mass flow controller for controlling the rate of the second sample flow through the reference chamber.

5. The analyzer of claim 4, further comprising:
   a third mass flow controller for controlling the rate of the flow of the carrier gas through the sample chamber; and
   a fourth mass flow controller for controlling the rate of the flow of the carrier gas through the reference chamber.

6. The analyzer of claim 5, further comprising an exhaust pump for drawing the first sample flow through the sample chamber and for drawing the second sample flow through the reference chamber.

7. The analyzer of claim 1, wherein the detector further comprises a thermal conductivity detector.

8. The analyzer of claim 1, wherein the detector further comprises an electron capture detector.

9. A method of measuring the amount of liquid water in an aerosol, comprising the steps of:
   providing a sample chamber;
   directing a first sample flow of the aerosol through the sample chamber at a first flow rate for a first time period;
   separating the liquid and solid components from the gaseous components of the first sample in the sample chamber;
   measuring the quantity of water contained in the sample chamber;
   providing a reference chamber substantially identical to the sample chamber;
   separating the liquid and solid components from the gaseous components of a second sample flow of the aerosol;
   directing the gaseous components of the second sample through the reference chamber at a second flow rate for a second time period;
   measuring the quantity of water contained in the reference chamber; and
   subtracting the amount of water measured in the reference chamber from the amount of water measured in the sample chamber to determiqe the amount of liquid water in the aerosol.

10. The method of claim 9, wherein the step of separating the liquid and solid components from the gaseous components of the first sample in the sample chamber further comprises:

providing a sample filter in the sample chamber for separating the liquid and solid components of the first sample from the gaseous components of the first sample; and providing a reference filter substantially identical to the sample filter in the reference chamber.

11. The method of claim 9, wherein the step of measuring the quantity of water contained in the sample chamber further comprises:

evaporating the liquid components of the first sample from the sample chamber with a carrier gas;

separating the water vapor from the evaporated components of the first sample with a chromatographic separation column; and measuring the quantity of water separated by the separation column.

12. The method of claim 9, wherein the step of measuring the quantity of water contained in the reference chamber further comprises:

evaporating any liquid components in the reference chamber with a carrier gas; and measuring the quality of water in the evaporated liquid components.

13. A method of measuring the amount of liquid water in an aerosol, comprising the steps of:

providing a sample chamber;

removing adsorbed water and water vapor from the sample chamber;

directing a first sample flow of the aerosol through the sample chamber at a first flow rate for a first time period;

separating the liquid and solid components from the gaseous components of the first sample in the sample chamber;

evaporating the liquid components of the first sample from the sample chamber by directing a flow of a carrier gas through the sample chamber;

separating the water vapor from the evaporated components of the first sample;

measuring the quantity of water vapor separated;

providing a reference chamber substantially identical to the sample chamber;

removing adsorbed water and water vapor from the reference chamber;

separating the liquid and solid components from the gaseous components of a second sample flow of the aerosol;

directing the gaseous components of the second sample through the reference chamber at a second flow rate for a second time period;

evaporating the liquid components from the reference chamber by directing a flow of a carrier gas through the reference chamber;

measuring the quantity of water vapor in the carrier gas from the reference chamber;

subtracting the amount of water measured in the reference chamber carrier gas from the amount of water measured in the sample chamber carrier gas to determine the amount of liquid water in the aerosol.

* * * * *